United States Patent
Erickson-Miller et al.

(10) Patent No.: US 8,476,249 B2
(45) Date of Patent: Jul. 2, 2013

(54) METHOD OF TREATING THROMBOCYTOPENIA

(75) Inventors: Connie L. Erickson-Miller, King of Prussia, PA (US); Michael Arning, Uxbridge (GB)

(73) Assignee: GlaxoSmithKline LLC, Philadelphia, PA (US)

(*) Notice: Subject to any disclaimer, the term of this patent is extended or adjusted under 35 U.S.C. 154(b) by 0 days.

(21) Appl. No.: 13/318,550

(22) PCT Filed: May 6, 2010

(86) PCT No.: PCT/US2010/033823
§ 371 (c)(1),
(2), (4) Date: Nov. 2, 2011

(87) PCT Pub. No.: WO2010/129738
PCT Pub. Date: Nov. 11, 2010

(65) Prior Publication Data
US 2012/0052055 A1  Mar. 1, 2012

(51) Int. Cl.
A61K 31/655 (2006.01)
A61P 7/00 (2006.01)
A61K 31/415 (2006.01)
A61K 31/44 (2006.01)
A61K 38/58 (2006.01)
A61K 38/37 (2006.01)

(52) U.S. Cl.
USPC .......... 514/150; 514/404; 514/253.1; 514/56; 514/161; 514/14.8; 514/314; 514/210.17; 514/230.8; 514/258.1; 514/253.09; 514/352; 514/13.7; 514/14.1; 514/14.3; 514/14.9

(58) Field of Classification Search
USPC ............... 514/150, 404, 253.1, 56, 161, 14.8, 514/314, 210.17, 230.8, 258.1, 253.09
See application file for complete search history.

(56) References Cited

U.S. PATENT DOCUMENTS

| | | | |
|---|---|---|---|
| 6,887,890 B2 | 5/2005 | Fujiwara et al. | |
| 7,026,334 B1 | 4/2006 | Takemoto et al. | |
| 2004/0077697 A1 | 4/2004 | Koshio et al. | |
| 2007/0129338 A1 | 6/2007 | Duffy et al. | |
| 2008/0233554 A1 | 9/2008 | Sehgal et al. | |
| 2010/0022542 A1 | 1/2010 | Takemoto et al. | |
| 2010/0222329 A1 | 9/2010 | Sugasawa et al. | |

FOREIGN PATENT DOCUMENTS

| | | |
|---|---|---|
| AU | 2003268687 | 4/2004 |
| EP | 0815869 | 1/1998 |
| EP | 1 104 674 | 8/2001 |
| EP | 1897888 | 3/2008 |
| WO | WO00/29104 | 5/2000 |
| WO | WO 01/07423 | 2/2001 |
| WO | WO 01/89457 | 11/2001 |
| WO | WO 02/59099 | 1/2002 |
| WO | WO 02/59100 | 1/2002 |
| WO | WO03/098992 | 12/2003 |
| WO | WO 2004/096154 | 11/2004 |
| WO | WO2005/009361 | 2/2005 |
| WO | WO 2005/118551 | 12/2005 |
| WO | WO 2006/047344 | 5/2006 |
| WO | WO 2007/062078 | 5/2007 |
| WO | WO 2007/106564 | 9/2007 |
| WO | WO2008/070583 | 6/2008 |

OTHER PUBLICATIONS

Afdhal, et al., *Journal of Hepatology*, 52:S460 (S459-S471), (2010).
Cwirla, et al., *Science*, 276:1696-1699 (1997).
Greene, "*Protective Groups in Organic Synthesis*", 1981, Table of Contents.
Hasegawa, et al., *Int. J. Immunopharmac*, 1996, vol. 18, No. 2, pp. 103-112.
Komatsu, et al., *Blood*, 1996, vol. 87, No. 11, pp. 4552-4560.
Kuter, et al., *Seminars in Hematology*, Apr. 2000, vol. 37, No. 2, pp. 41-49.
Lamb, et al., *Nucleic Acids Research*, 1995, vol. 23, No. 16, pp. 3283-3289.
Laurenz, et al., *Comp. Biochem Physiol.*, 1997, vol. 116A, No. 4, pp. 369-377.
Maynard, et al., *J Thromb Thrombolysis*, 29:159-166 (2010).
McDonald, et al., *Am. J. of Pediatric Hematology/Oncology*, 1992, vol. 14, No. 1, pp. 8-21.
Metcalf, et al., *Nature*, Jun. 16, 1994, vol. 369, pp. 519-520.
Seidel, et al., *Proc. Natl. Acad. Sci. USA*, Mar. 1995, vol. 92, pp. 3041-3045.
Shiotsu, et al., *Experimental Hematology*, 1998, vol. 26, pp. 1195-1201.
Vigon, et al., *Proc. Natl. Acad. Sci. USA*, Jun. 1992, vol. 89, pp. 5640-5644.
Zecchini, et al., *Journal of Hepatology*, 52 :S459-S471, 1186 :S460 (2010).

*Primary Examiner* — Savitha Rao
(74) *Attorney, Agent, or Firm* — Wayne J. Dustman; Edward R. Gimmi

(57) ABSTRACT

Invented is a method of treating thrombocytopenia in a human, in need thereof which comprises the in vivo administration of a therapeutically effective amount of a peptide or a non-peptide TPO receptor agonist and an anti-clotting agent or agents, and optional further active ingredients, to such human.

4 Claims, No Drawings

METHOD OF TREATING THROMBOCYTOPENIA

This application is a 371 of International Application No. PCT/US2010/033823, filed 6 May 2010, which claims priority to U.S. Provisional Application 61/176,303 filed 7 May 2009.

FIELD OF THE INVENTION

This invention relates to a method of treating thrombocytopenia in a human by the in vivo administration of a peptide or a non-peptide thrombopoietin (TPO) receptor agonist and an anti-clotting agent or agents, and pharmaceutical compositions containing the same. Suitably, the method relates to methods of treating thrombocytopenia by administration of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid or a pharmaceutically acceptable salt thereof, suitably the bis-(monoethanolamine) salt, (hereinafter the bis-(monoethanolamine) salt is Compound A; which is a compound is represented by Structure I:

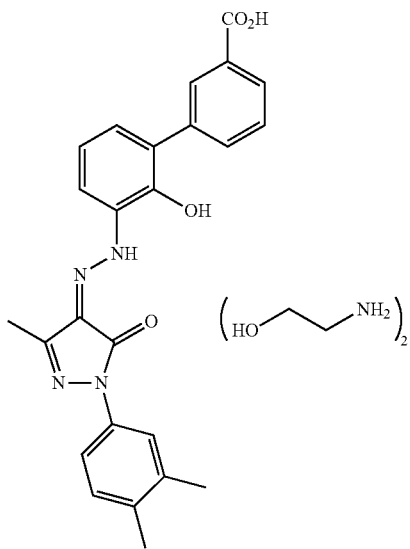

and the corresponding salt free compound is Compound B); and an anti-clotting agent or agents.

Suitably this invention relates to a method of administering a peptide or a non-peptide thrombopoietin (TPO) receptor agonist which comprises co-administration with an anti-clotting agent or agents.

Suitably this invention relates to a novel combination of a peptide or a non-peptide thrombopoietin (TPO) receptor agonist and an anti-clotting agent or agents, and optional further active ingredients.

BACKGROUND OF THE INVENTION

Thrombopoietin (TPO) has been shown to be the main humoral regulator in situations involving thrombocytopenia. See, e.g., Metcalf Nature 369:519-520 (1994). TPO has been shown in several studies to increase platelet counts, increase platelet size, and increase isotope incorporation into platelets of recipient animals. Because platelets (thrombocytes) are necessary for blood clotting and when their numbers are very low a patient is at risk of death from catastrophic hemorrhage, TPO is considered to have potential useful applications in both the diagnosis and the treatment of various hematological disorders, for example, diseases primarily due to platelet defects. In addition, studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See e.g., McDonald (1992) Am. J. Ped. Hematology/Oncology 14: 8-21 (1992).

The slow recovery of platelet levels in patients suffering from thrombocytopenia is a serious problem, and has lead to the search for small molecule non-peptide TPO receptor agonists that are able to accelerate platelet regeneration. (e.g. see, International Application Number PCT/US01/16863, having International Filing Date May 24, 2001, which specifically discloses Compound B, in Example 3, and the use of non-peptide TPO receptor agonists in combination with further active ingredients). International Application Number PCT/US01/16863 specifically includes the treatment of thrombocytopenia wherein the thrombocytopenia is due to: myelosuppression, organ transplant, bone marrow transplant, stem cell transplant, liver transplant, idiopathic thrombocytopenia purpura (ITP), myelodysplastic syndromes (MDS), aplastic anemia. leukemia, viral infection, fungal infection, microbial infection. parasitic infection, liver dysfunction, surgical procedures, treatment with antiviral agents, and treatment with antibiotic agents.

Compound A is disclosed in International Application No. PCT/US03/16255, having an International filing date of May 21, 2003; International Publication Number WO 03/098002 and an International Publication date of Dec. 4, 2003.

Non-peptide TPO receptor agonists, including Compound A, are disclosed for the treatment of degenerative diseases/injuries in International Application No. PCT/US04/013468, having an International filing date of Apr. 29, 2004; International Publication Number WO 04/096154 and an International Publication date of Nov. 11, 2004.

Peptide and non-peptide thrombopoietin (TPO) receptor agonist, in addition to raising platelet levels, can potentiate the formation of blood clots in otherwise unbroken/untraumatized veins and arteries.

It would be advantageous to provide an improved method of treating thrombocytopenia.

It would be advantageous to provide an improved method of administering peptide or non-peptide thrombopoietin (TPO) receptor agonist.

SUMMARY OF THE INVENTION

This invention relates to a method of treating thrombocytopenia in a human in need thereof which comprises the in vivo administration to such human of a therapeutically effective amount of a peptide or non-peptide thrombopoietin (TPO) receptor agonist and an anti-clotting agent or agents, and optional further active ingredients.

This invention relates to a method of administering a peptide or a non-peptide thrombopoietin (TPO) receptor agonist to a human in need thereof which comprises administering to such human a therapeutically effective amount of a peptide or non-peptide thrombopoietin (TPO) receptor agonist and an anti-clotting agent or agents, and optional further active ingredients.

The invention relates to novel combinations of a peptide or non-peptide thrombopoietin (TPO) receptor agonist and an anti-clotting agent or agents, and optional further active ingredients.

Included among the non-peptide TPO receptor agonists of the invention are compounds of Formula (I):

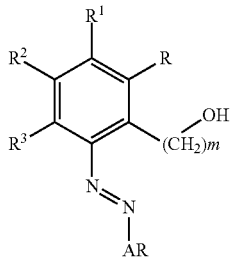

wherein:

R, $R^1$, $R^2$ and $R^3$ are each independently selected from hydrogen, $C_{1-6}$alkyl, $-(CH_2)_pOR^4$, $-C(O)OR^4$, formyl, nitro, cyano, halogen, aryl, substituted aryl, substituted alkyl, $-S(O)_nR^4$, cycloalkyl, $-NR^5R^6$, protected —OH, $-CONR^5R^6$, phosphonic acid, sulfonic acid, phosphinic acid, $-SO_2NR^5R^6$, and a heterocyclic methylene substituent as represented by Formula (III),

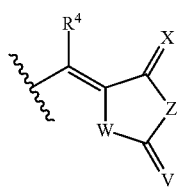

where, p is 0-6, n is 0-2,

V, W, X and Z are each independently selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, $R^4$ is selected from: hydrogen, alkyl, cycloalkyl, $C_1$-$C_{12}$aryl, substituted alkyl, substituted cycloalkyl and substituted $C_1$-$C_{12}$aryl, and $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen;

m is 0-6; and

AR is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, $-C(O)OR^4$, $-C(O)NR^{10}R^{11}$, $-S(O)_2NR^{10}R^{11}$, $-S(O)_nR^4$ and protected —OH, where n is 0-2, $R^4$ is hydrogen, alkyl, cycloalkyl, $C_1$-$C_{12}$aryl, substituted alkyl, substituted cycloalkyl and substituted $C_1$-$C_{12}$aryl, and $R^{10}$ and $R^{11}$ are independently hydrogen, cycloalkyl, $C_1$-$C_{12}$aryl, substituted cycloalkyl, substituted $C_1$-$C_{12}$aryl, alkyl or alkyl substituted with one or more substituents selected from the group consisting of: alkoxy, acyloxy, aryloxy, amino, N-acylamino, oxo, hydroxy, $-C(O)OR^4$, $-S(O)_nR^4$, $-C(O)NR^4R^4$, $-S(O)_2NR^4R^4$, nitro, cyano, cycloalkyl, substituted cycloalkyl, halogen, aryl, substituted aryl and protected —OH, or $R^{10}$ and $R^{11}$ taken together with the nitrogen to which they are attached represent a 5 to 6 member saturated ring containing up to one other heteroatom selected from oxygen and nitrogen, where $R^4$ is as described above and n is 0-2;

or a pharmaceutically acceptable salt thereof;

provided that at least one of R, $R^1$, $R^2$ and $R^3$ is a substituted aryl group or a heterocyclic methylene substituent as represented in Formula (III).

Included among the peptide TPO receptor agonists of the invention is the known protein AMG 531.

DETAILED DESCRIPTION OF THE INVENTION

Because peptide and non-peptide thrombopoietin (TPO) receptor agonist can potentiate the formation of blood clots in otherwise unbroken or untraumatized veins and arteries an improved method of treating thrombocytopenia and/or administering such peptide and non-peptide thrombopoietin (TPO) receptor agonist is co-administer with an anti-clotting agent.

This invention relates to a method of treating thrombocytopenia in a human in need thereof which comprises the in vivo administration to such human a therapeutically effective amount of a non-peptide thrombopoietin (TPO) receptor agonist of Formula (I) and an anti-clotting agent or agents, and optional further active ingredients.

This invention relates to a method of treating thrombocytopenia in a human in need thereof which comprises the in vivo administration to such human a therapeutically effective amount of the peptide thrombopoietin (TPO) receptor agonist AMG 531 and an anti-clotting agent or agents, and optional further active ingredients.

This invention relates to a method of administering a non-peptide thrombopoietin (TPO) receptor agonist of Formula (I) to a human in need thereof which comprises the co-administration to such human a therapeutically effective amount of a non-peptide thrombopoietin (TPO) receptor agonist of Formula (I) and an anti-clotting agent or agents, and optional further active ingredients.

This invention relates to a method of administering the peptide thrombopoietin (TPO) receptor agonist AMG-531 to a human in need thereof which comprises administering to such human a therapeutically effective amount of the thrombopoietin (TPO) receptor agonist AMG-531 and an anti-clotting agent or agents, and optional further active ingredients. Suitably, when AMG-531 is used in accordance with this invention, AMG-531 is administered conventionally in conventional amounts. When referring to AMG-531, the present invention means the compound known by the generic name romiplostim and that is marketed under the trade name Nplate™. AMG-531 is claimed in U.S. Pat. Nos. 6,835,809 and 7,189,827. AMG-531 can be prepared by and is used according to known methods such as described in U.S. Pat. Nos. 6,835,809 and 7,189,827.

The invention relates to novel combinations of a non-peptide thrombopoietin (TPO) receptor agonist of Formula (I) and an anti-clotting agent or agents, and optional further active ingredients.

The invention relates to novel combinations of the peptide thrombopoietin (TPO) receptor agonist AMG-531 and an anti-clotting agent or agents, and optional further active ingredients.

This invention relates to a method of treating thrombocytopenia in a human in need thereof which comprises the in vivo administration to such mammal of a therapeutically effective amount of 1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid, or a pharmaceutically acceptable salt thereof and an anti-clotting agent or agents, and optional further active ingredients.

This invention relates to a method of administering 1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid, or a pharmaceutically acceptable salt thereof to a human in need thereof which comprises the co-administration to such human a therapeutically effective amount of 1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid, or a pharmaceutically acceptable salt thereof and an anti-clotting agent or agents, and optional further active ingredients.

The invention relates to novel combinations of 1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid, or a pharmaceutically acceptable salt thereof and an anti-clotting agent or agents, and optional further active ingredients.

Included among compounds of Formula (I) that are useful in the current invention are those having Formula (VI):

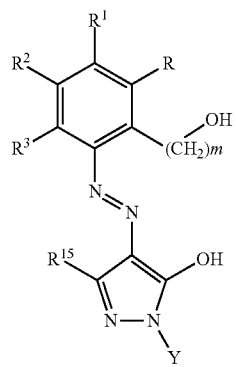

(VI)

wherein:
R, $R^1$, $R^2$ and $R^3$ are each independently selected from hydrogen, $C_{1-6}$alkyl, $C_{1-6}$alkoxy, —$(CH_2)_pOR^4$, —$C(O)OR^4$, formyl, nitro, cyano, halogen, aryl, substituted aryl, substituted alkyl, —$S(O)_nR^4$, cycloalkyl, —$NR^5R^6$, protected —OH, —$CONR^5R^6$, phosphonic acid, sulfonic acid, phosphinic acid and —$SO_2NR^5R^6$, where
p is 0-6,
n is 0-2, $R^4$ is hydrogen, alkyl, cycloalkyl, $C_1$-$C_{12}$aryl, substituted alkyl, substituted cycloalkyl and substituted $C_1$-$C_{12}$aryl, and $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen;

$R^{15}$ is selected from the group consisting of alkyl, $C_1$-$C_{12}$aryl, hydroxy, alkoxy, substituted alkyl, substituted $C_1$-$C_{12}$aryl and halogen;

m is 0-6; and

Y is selected from alkyl, substituted alkyl and a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, $C_1$-$C_{12}$aryl, substituted cycloalkyl, substituted $C_1$-$C_{12}$aryl, hydroxy, aryloxy, alkoxy, cycloalkyl, nitro, cyano, halogen and protected —OH;

or a pharmaceutically acceptable salt thereof;

provided that at least one of R, $R^1$, $R^2$ and $R^3$ is a substituted aryl group.

Included among the non-peptide TPO agonist compounds useful in the present invention are those having Formula (VI) in which, either:
R is a substituted aryl; and $R^1$ is hydrogen;
or:
R is hydrogen; and $R^1$ is a substituted aryl;
and in either case:
$R^2$ and $R^3$ are each independently selected from hydrogen, $C_{1-6}$alkyl, $C_{1-6}$alkoxy, nitro, cyano, halogen, aryl, substituted aryl, substituted alkyl, cycloalkyl, phosphonic acid, phosphinic acid and sulfonic acid;

$R^{15}$ is selected from the group consisting of alkyl, substituted alkyl, $C_1$-$C_{12}$aryl, alkoxy and halogen;

m is 0-4; and

Y is selected from,
phenyl, pyridinyl and pyrimidinyl, where the phenyl, pyridinyl and pyrimidinyl are optionally substituted with from one to three substituents selected from the group consisting of: alkyl, substituted alkyl, $C_1$-$C_{12}$aryl, substituted $C_1$-$C_{12}$aryl, alkoxy and halogen;

or a pharmaceutically acceptable salt thereof.

Included among the compounds useful in the present invention are those having Formula (VI) in which,
R is a substituted $C_1$-$C_{12}$aryl; and
$R^1$ is hydrogen;
$R^2$ and $R^3$ are each independently selected from hydrogen, $C_{1-6}$alkyl, $C_{1-6}$alkoxy, nitro, cyano, halogen, substituted alkyl and cycloalkyl;
$R^{15}$ is selected from the group consisting of alkyl, substituted alkyl, $C_1$-$C_{12}$aryl, alkoxy and halogen;
m is 0-2; and
Y is selected from,
phenyl, pyridinyl and pyrimidinyl, where the phenyl, pyridinyl and pyrimidinyl are optionally substituted with from one to three substituents selected from the group consisting of: alkyl, substituted alkyl, $C_1$-$C_{12}$aryl, substituted $C_1$-$C_{12}$aryl, alkoxy and halogen;

or a pharmaceutically acceptable salt thereof.

Included among the compounds useful in the present invention are those having Formula (VI) in which, R is a substituted phenyl or pyridinyl ring; and $R^1$ is hydrogen;

$R^2$ and $R^3$ are each independently selected from hydrogen, $C_{1-6}$alkyl, substituted alkyl and halogen;

$R^{15}$ is selected from the group consisting of $C_{1-4}$alkyl, $C_{1-4}$alkoxy, $C_1$-$C_{12}$aryl and halogen;

m is 0; and

Y is selected from,
phenyl, pyridinyl and pyrimidinyl, where the phenyl, pyridinyl and pyrimidinyl is optionally substituted with from one to three substituents selected from the group consisting of: alkyl, substituted alkyl, $C_1$-$C_{12}$aryl, substituted $C_1$-$C_{12}$aryl, alkoxy and halogen;

or a pharmaceutically acceptable salt thereof.

Included among the non-peptide TPO agonist compounds useful in the present invention are:

3'-{N'-[1'-(3,4-Dimethylphenyl)-3-methyl-5-oxo-1,5-dihydropyrazol-4-ylidene]hydrazino}-2'-hydroxybiphenyl-3-carboxylic acid;

3-{N'-[1'-(3,4-dimethylphenyl)-3-methyl-5-oxo-1,5-dihydropyrazol-4-ylidene]hydrazino}-2-hydroxy-3'-(tetrazol-5-yl)biphenyl;

1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid;

3'-{N'-[1'-(3,5-Dimethyl-phenyl)-2-oxo-6-trifluoromethyl-1,2-dihydro-indol-3-ylidene]-hydrazino}-2'-hydroxybiphenyl-3-carboxylic acid;

2'-hydroxy-3'-{N'-[2-oxo-1-(4-propyl-phenyl)-1,2-dihydro-indol-3-ylidene]-hydrazino}-biphenyl-4-carboxylic acid; and or a pharmaceutically acceptable salt thereof.

Included among the non-peptide TPO receptor agonists of the invention are the non-peptide compounds described in:

WO 02/59099;
WO 02/59100;
EP 1 207 155;
EP 1 253 142A1;
WO 01/92211 A1;
WO 01/53267-A1;
WO 03/62233
WO 02/62775
EP 1 104 674-A1; and
WO 01/07423-A1.

Included among the compounds of the above listed applications that are useful in the present invention are:

N-[4-(5-bromo-2-thienyl)-1,3-thiazol-2-yl]-4-[(Z)-(2,4-dioxo-1,3-thiazolidin-5-ylidene)methyl]benzamide;

N-[4-(3,4-dimethylphenyl)-1,3-thiazol-2-yl]-4-[(Z)-(2,4-dioxo-1,3-thiazolidin-5-ylidene)methyl]benzamide;

N-{4-[4-(1,1-dimethylethyl)phenyl]-1,3-thiazol-2-yl}-4-[(Z)-(2,4-dioxo-1,3-thiazolidin-5-ylidene)methyl]benzamide;

N-[4-(3,4-dichlorophenyl)-1,3-thiazol-2-yl]-4-[(Z)-(2,4-dioxo-1,3-thiazolidin-5-ylidene)methyl]benzamide; and (2E)-3-[4-({[4-(3,4-dichlorophenyl)-1,3-thiazol-2-yl]amino}carbonyl)phenyl]-2-methyl-2-propenoic acid;

or a pharmaceutically acceptable salt thereof.

Included among the non-peptide TPO receptor agonists of the invention are the non-peptide compounds described in:

WO 99/11262.

Included among the non-peptide TPO receptor agonists of the invention are the non-peptide compounds described in:

International Application No. PCT/US05/018924, having an International filing date of May 27, 2005; International Publication Number WO 05/118551 and an International Publication date of Dec. 15, 2005, International Application No. PCT/US05/038055, having an International filing date of Oct. 21, 2005; International Publication Number WO 06/047344 and an International Publication date of May 4, 2006, International Application No. PCT/US06/045129, having an International filing date of Nov. 21, 2006; International Publication Number WO 07/062,078 and an International Publication date of May 31, 2007, and International Application No. PCT/US07/006,547, having an International filing date of Mar. 14, 2007; International Publication Number WO 07/106,564 and an International Publication date of Sep. 20, 2007.

The compounds that are final products in WO 05/118551, WO 06/047344, WO 07/062,078 and WO 07/106,564 are useful in the present invention, these compounds are included herein by reference.

The compound that is the product of Example 4 in WO 07/106,564, 3'-{N'-[1-(3,5-Dimethyl-phenyl)-2-oxo-6-trifluoromethyl-1,2-dihydro-indol-3-ylidene]-hydrazino}-2'-hydroxybiphenyl-3-carboxylic acid, as the salt free compound or in the form of a pharmaceutically acceptable salt, is a non-peptide TPO agonist compound useful in the present invention.

The compound that is the product of Example 6 in WO 07/106,564, 2'-hydroxy-3'-{N'-[2-oxo-1-(4-propyl-phenyl)-1,2-dihydro-indol-3-ylidene]-hydrazino}-biphenyl-4-carboxylic acid, as the salt free compound or in the form of a pharmaceutically acceptable salt, is a non-peptide TPO agonist compound useful in the present invention.

Included among the non-peptide TPO receptor agonists of the invention is the non-peptide compound described in:

International Application No. PCT/JP03/012419, having an International filing date of Sep. 29, 2003; International Publication Number WO 04/029049 and an International Publication date of Apr. 8, 2004, 2005.

The compound that is the final product in WO 04/029049, both the salt and non-salt forms, is useful in the present invention, these compounds are included herein by reference.

Suitably, the compound that is the final product in WO 04/029049 is 1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid, as the salt free compound (hereinafter Compound E), or in the form of a pharmaceutically acceptable salt thereof. Suitably, the salt is a maleic acid salt (hereinafter Compound F). The structure of Compound F is indicated below.

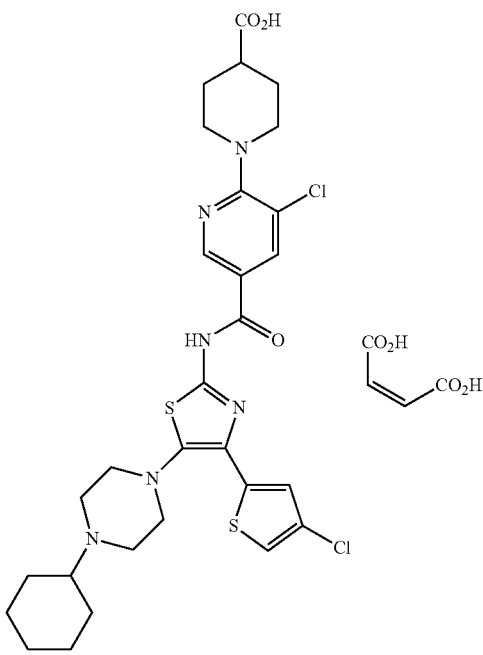 [SMILES: O=C(Nc1nc(-c2cc(Cl)cs2)c(N2CCN(C3CCCCC3)CC2)s1)c1cnc(N2CCC(C(=O)O)CC2)c(Cl)c1 ; O=C(O)/C=C\C(=O)O]

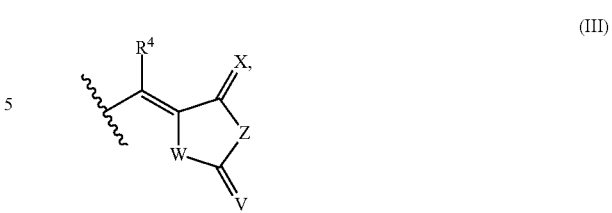

Peptide and non-peptide TPO receptor agonists are included in the pharmaceutical compositions of the invention and used in the methods of the invention.

By the term "protected hydroxy" or "protected —OH" as used herein, is meant the alcoholic or carboxylic-OH groups which can be protected by conventional blocking groups in the art such as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1$-$C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

When referring to compounds of Formula (I) and (II), the term "substituted" as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, alkyl, amino, N-acylamino, hydroxy, —$(CH_2)_gC(O)OR^8$, —$S(O)_n$ $R^8$, nitro, tetrazole, cyano, oxo, halogen, trifluoromethyl, protected —OH and a heterocyclic methylene substituent as represented by Formula (III), where g is 0-6; $R^8$ is hydrogen or alkyl; $R^{20}$ is selected form hydrogen, $C_1$-$C_4$alkyl, aryl and trifluoromethyl; $R^{21}$ and $R^{22}$ are independently selected form hydrogen, $C_1$-$C_4$alkyl, aryl and trifluoromethyl; V, W, X and Z are each independently selected from O, S, and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl; and n is 0-2.

When referring to compounds of Formula (V) and (VI), the term "substituted" as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, alkyl, amino, N-acylamino, hydroxy, —$(CH_2)_gC(O)OR^8$, —$S(O)_n$ $R^8$, nitro, tetrazole, cyano, oxo, halogen, trifluoromethyl and protected —OH, where g is 0-6, $R^8$ is hydrogen or alkyl, $R^{20}$ is selected form hydrogen, $C_1$-$C_4$alkyl, aryl and trifluoromethyl, and $R^{21}$ and $R^{22}$ are independently selected form hydrogen, $C_1$-$C_4$alkyl, aryl and trifluoromethyl, and n is 0-2.

By the term "alkoxy" as used herein is meant -Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$-$C_{12}$.

Examples of cycloalkyl and substituted cycloalkyl substituents as used herein include: cyclohexyl, 4-hydroxy-cyclohexyl, 2-ethylcyclohexyl, propyl 4-methoxycyclohexyl, 4-methoxycyclohexyl, 4-carboxycyclohexyl, cyclopropyl and cyclopentyl.

By the term "acyloxy" as used herein is meant —OC(O) alkyl where alkyl is as described herein. Examples of acyloxy substituents as used herein include: —$OC(O)CH_3$, —$OC(O)$ $CH(CH_3)_2$ and —$OC(O)(CH_2)_3CH_3$.

By the term "N-acylamino" as used herein is meant —$N(H)C(O)$alkyl, where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant -Oaryl where aryl is phenyl, naphthyl, 3,4-methylenedioxyphenyl, pyridyl or biphenyl optionally substituted with one or more substituents selected from the group consisting of: alkyl, hydroxyalkyl, alkoxy, trifluoromethyl, acyloxy, amino, N-acylamino, hydroxy, —$(CH_2)_gC(O)OR^8$, —$S(O)_nR^8$, nitro, cyano, halogen and protected —OH, where g is 0-6, $R^8$ is hydrogen or alkyl, and n is 0-2. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain, and unless otherwise defined, the carbon chain will contain from 1 to 12 carbon atoms. Examples of alkyl substituents as used herein include: —$CH_3$, —$CH_2$—$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$, —$CH(CH_3)$—$CH_2$—$CH_3$, —$CH=CH_2$, and —$C\equiv C$—$CH_3$.

By the term "anti-clotting agent" as used herein is meant a compound or other therapeutic agent that is known or is found to prevent or lessen the incidence of blood clots over a defined period of time when administered to a mammal, including a human, including preventing or lessening the incidence of blood clots over a defined period of time when co-administered to a mammal, including a human with a peptide or a non-peptide thrombopoietin (TPO) receptor agonist. Examples of "anti-clotting agents" for use herein with the peptide and non-peptide thrombopoietin (TPO) receptor agonist include but are not limited to the following:

Anti-Coagulant Drugs
Heparin or enoxaparin (Calciparin®, Liquaemine®)
Warfarin (suitably Coumadin®)
Anti-Platelet Drugs
Aspirin
Clopidogrel (Plavix®)
Ticlopidine (Ticlid®)
Dipyridamole
Prasugrel (Effient)
Thrombolytic Agents
Tissue plasminogen activator (Activase®)
Direct Thrombin Inhibitors
Hirudin
lepirudin
argatroban
Ximelagatran
Bivalirudin
Dabigatran etexilate
rivaroxaban (BAY 59-7939), apixaban (BMS), YM150 (Astellas), DU-176b (Daiichi),
LY517717 (Lilly), and PRT054021 (Portola). Rivaroxaban (Bay 59-7939)
Direct Factor Xa Inhibitors
Fondaparinux—synthetic pentasaccharide
Idraparinux
tick anticoagulant peptide[ ](TAP)
antistatin
DX 9065a
Org31540/SR90107A—a synthetic PS (pentasaccharide)
Factor IXa Inhibitors
Active-site blocked Factor IXa
Monoclonal anti-Factor IXa
Protein C Modulators
Protein C Derivatives (recombinant protein C)
Recombinant Thrombomodulin
Inhibitors of FactorVIIa/Tissue Factor Path
Tissue factor inhibitors—mutant tissue factor
Factor VIIa inhibitors (Factor VIIai)
Factor VIIa/tissue factor blockers (TFPI, NAPc2)

By the term "treating" and derivatives thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing blood clots, or when a subject has a history, including a family history, of blood clots.

As used herein, the term "effective amount" and derivatives thereof means that amount of a drug or pharmaceutical agent that will elicit the biological or medical response of a tissue, system or human that is being sought, for instance, by a researcher or clinician. Furthermore, the term "therapeutically effective amount" and derivatives thereof means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "thrombotic event" and derivatives thereof means the obstruction of an artery or vein by a blood clot. Examples of thrombotic events as used herein includes but is not limited to: i) the formation of an embolus, and ii) any form of thrombosis including: portal vein thrombosis, the blocking or partial blocking of a vein or artery leading to a heart attack or myocardial infarction, stroke, arteriosclerosis, or atherosclerosis. As used herein the term thrombotic events can include the blocking or partial blocking in the portal vein system.

By the phrase "non-peptide" as used herein is meant a chemical compound, or a protein or peptide not comprised primarily of natural amino acids. Suitably, the "non-peptide" is a small molecule chemical compound having a molecular weight under 1,500 daltons, suitably under 1,000 daltons.

By the term "primarily" as used above is meant about 60% by weight of naturally occurring amino acid residue.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of the compounds of the invention.

Certain compounds described herein may form a solvate which is understood to be a complex of variable stoichiometry formed by a solute (for example, a compound of Formula I of a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

The compounds of the invention are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

The pharmaceutically acceptable salts of the compounds of the invention are readily prepared by those of skill in the art.

The compounds of Formula I are disclosed and claimed, along with pharmaceutically acceptable salts, hydrates, solvates and esters thereof, as being useful as an agonist of the TPO receptor, particularly in enhancing platelet production and particularly in the treatment of thrombocytopenia, in International Application No. PCT/US01/16863, having an International filing date of May 24, 2001; International Publication Number WO 01/89457 and an International Publication date of Nov. 29, 2001, the entire disclosure of which is hereby incorporated by reference. Compounds of Formulas I and pharmaceutically acceptable salts, hydrates, solvates and esters thereof, are prepared as described in International Application No. PCT/US01/16863. The bis-(monoethanolamine) salt of a compound described in International Application No. PCT/US01/16863, is described in International Application No. PCT/US03/16255, having an International filing date of May 21, 2003; International Publication Number WO 03/098992 and an International Publication date of Dec. 4, 2003.

When referring to the treatment of thrombocytopenia, the term "co-administering" and derivatives thereof as used herein is meant either simultaneous administration or any manner of separate sequential administration of a peptide or non-peptide TPO receptor agonist, as described herein, and an anti-clotting agent or agents, as described herein, and optional further active agents. Preferably, if the administration is not simultaneous, the compounds are administered in a close time proximity to each other. Furthermore, it does not matter if the compounds are administered in the same dosage form, e.g. one compound may be administered topically and another compound may be administered orally.

When referring to a method for administering a peptide or non-peptide TPO receptor agonist, as described herein, and an anti-clotting agent or agents, as described herein, the term "co-administering" and derivatives thereof as used herein is meant either simultaneous administration or any manner of separate sequential administration of the peptide or non-peptide TPO receptor agonist and anti-clotting agent or agents, and optional further active agents. Preferably, if the administration is not simultaneous, the compounds are administered in a close time proximity to each other. Furthermore, it does not matter if the compounds are administered in the same dosage form, e.g. one compound may be administered topically and another compound may be administered orally.

By the term "combination" as used herein is meant either simultaneous administration or any manner of separate sequential administration of a peptide or non-peptide TPO receptor agonist and anti-clotting agent or agents, and optional further active agents. Preferably, if the administration is not simultaneous, the compounds are administered in a close time proximity to each other. Furthermore, it does not matter if the compounds are administered in the same dosage form, e.g. one compound may be administered topically and another compound may be administered orally. Regarding the present invention, a "combination" requires, at a minimum, one peptide or non-peptide TPO receptor agonist, as described herein, and an anti-clotting agent. Also contemplated for use herein is the optional co-administration of a further active agent or agents with the combination.

TPO is known to have various effects including anti-apototic/survival effects on megakaryocytes, platelets and stem cells, and proliferative effects on stem cells and megakaryocytic cells (Kuter D. J. Seminars in Hematology, 2000, 37, 41-9). These TPO activities effectively increase the number of stem and progenitor cells so that there is synergistic effects when TPO is used in conjunction with other cytokines that induce differentiation.

The non-peptide TPO receptor agonists of the current invention are also useful in acting on cells for survival and/or proliferation in conjunction with other agents known to act on cells for survival and/or proliferation. Such other agents, or "further active ingredients" as used herein when referring to administration with TPO agonist compounds, include but are not limited to: G-CSF, GM-CSF, TPO, M-CSF, EPO, Gro-beta, IL-11, SCF, FLT3 ligand, LIF, IL-3, IL-6, IL-1, Progenipoietin, NESP, SD-01, or IL-5 or a biologically active derivative of any of the aforementioned agents, KT6352 (Shiotsu Y. et al., *Exp. Hemat.* 1998, 26, 1195-1201), uteroferrin (Laurenz J C., et al. *Comp. Biochem. & Phys., Part A. Physiology.,* 1997, 116, 369-77), FK23 (Hasegawa T., et al. *Int. J. Immunopharm.,* 1996, 18 103-112) and other molecules identified as having anti-apoptotic, survival or proliferative properties for stem cells, progenitor cells, or other cells expressing TPO Receptors.

One skilled in the art can readily determine by known methods if a compound is a non-peptide TPO receptor agonist and thus included within the scope of the current invention. By way of example, the following assays can be employed:

Luciferase Assay

Compounds are tested for potency as agonists of the TPO receptor in a Luciferase assay such as described in Lamb, et al., *Nucleic Acids Research* 23: 3283-3289 (1995) and Seidel, et al., *Proc. Natl. Acad. Sci.*, USA 92: 3041-3045 (1995) by substituting a TPO-responsive BaF3 cell line (Vigon et al. *Proc. Natl. Acad. Sci. USA* 1992, 89, 5640-5644) for the HepG2 cells utilized therein. The murine BaF3 cells express TPO receptors and closely match the pattern of STAT (signal transducers and activators of transcription) activation observed in primary murine and human bone marrow cells.

Proliferation Assay

Compounds are tested in an in vitro proliferation assay using the human UT7TPO cell line. UT7TPO cells are a human megakaryoblastic cell line that express Tpo-R, whose survival and growth is dependent on the presence of TPO (Komatsu et al. Blood 1996, 87, 4552).

Differentiation Assay

Compounds are tested for their ability in stimulating the maturation of megakaryocytes from human bone marrow cells. In this assay, purified human CD34+ progenitor cells are incubated in liquid culture with test compounds for 10 days and the number of cells expressing the transmembrane glycoprotein CD41 (gpIIb), a megakaryocytic marker, is then measured by flow cytometry (see Cwirla, S. E. et al Science, 1997, 276, 1696).

A TPO receptor agonist of the present invention, 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine) or eltrombopag, is indicated as being associated with thrombotic events, specifically in the portal vein system, in Afdhal et al., *Journal of Hepatology* (2010) Vol. 52, S459 to S471-#1185 at S460. An anticlotting agent of the invention, enoxaparin, is indicated as reducing the occurrence of portal vein thrombosis in Zecchini et al., *Journal of Hepatology* (2010) Vol. 52, S459 to S471 #1186 at S460.

The ability of the compounds and combinations of the current invention to treat thrombocytopenia and/or decrease the incidence of blood clots can be determined by those of skill in the art by known methods such as described in Maynard et al., *J Thromb Thrombolysis* (2010) 29: 159 to 166.

The presently invented combinations of TPO receptor agonists and anti-clotting agents can be tested and/or optimized according to known methods such as described in Maynard et al., *J Thromb Thrombolysis* (2010) 29: 159 to 166.

The compounds or combinations of the current invention are generally administered as pharmaceutical compositions or preparations.

The pharmaceutical compositions of the present invention may be administered to a patient in need thereof by any conventional route of administration, including, but not limited to, intravenous, intramuscular, oral, subcutaneous, intradermal, and parenteral.

The compounds or combinations of the current invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the pharmaceutically active compounds in a pharmaceutical dosage unit as described above will be an efficacious, nontoxic quantity preferably selected from the range of 0.001-100 mg/kg of active compound, preferably 0.002-50 mg/kg. When treating a human patient in need of a non-peptide TPO receptor agonist, the selected dose is administered preferably from 1-6 times daily, orally or parenterally. Preferred forms of parenteral administration include topically, rectally, transdermally, by injection and continuously by infusion. Oral dosage units for human administration suitably contain from 0.05 to 3500 mg, suitably from 0.1 to 3000 mg, suitably from 10 to 200 mg of active compound. Oral administration, which uses lower dosages is preferred. Parenteral administration, at high dosages, however, also can be used when safe and convenient for the patient.

As used herein, 3'-[(2Z)[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid and 3'-{N'-[4'-(3,4-Dimethylphenyl)-3-methyl-5-oxo-1,5-dihydropyrazol-4-ylidene]hydrazino}-2'-hydroxybiphenyl-3-carboxylic acid, refer to the same compound.

Suitably, when the compound 3'-{N'-[1'-(3,4-Dimethylphenyl)-3-methyl-5-oxo-1,5-dihydropyrazol-4-ylidene]hydrazino}-2'-hydroxybiphenyl-3-carboxylic acid, or a salt thereof, suitably the bis-(monoethanolamine) salt or Compound A, is used in accordance with this invention, the amount of compound administered will be from 25 mg to 150 mg, suitably from 25 mg to 125 mg, suitably from 25 mg to 100 mg, suitably the amount will be selected from: 25 mg, 50, mg, 75 mg, 100 mg, 125 mg, and 150 mg. Suitably, the selected dose will be administered from 1 to 3 times a day, suitably once a day. The amounts of compound indicated for administration are expressed in the amount of free or unsalted compound.

Suitably, when the compound 3'-{N'-[1'-(3,4-Dimethylphenyl)-3-methyl-5-oxo-1,5-dihydropyrazol-4-ylidene]hydrazino}-2'-hydroxybiphenyl-3-carboxylic acid, or a salt thereof, suitably the bis-(monoethanolamine) salt or Compound A, is used in accordance with this invention, the amount of compound administered will be 12.5 mg. Suitably, the selected dose will be administered from 1 to 3 times a day, suitably once a day. The amounts of compound indicated for administration are expressed in the amount of free or unsalted compound.

Optimal dosages of the presently invented compounds and combinations to be administered may be readily determined by those skilled in the art, and will vary with the particular compounds or combination in use, the strength of the preparation, the mode of administration, and the advancement of the disease condition. Additional factors depending on the particular patient being treated will result in a need to adjust dosages, including patient age, weight, diet, and time of administration.

The method of this invention of treating thrombocytopenia in humans comprises the in vivo administration to a subject in need thereof a therapeutically effective amount of a pharmaceutically active combination of the present invention.

The method of this invention of treating thrombocytopenia in humans comprises the in vivo administration to a subject in need thereof a therapeutically effective amount of a peptide or non-peptide TPO agonist and an anti-clotting agent or agents, and optionally further active ingredients.

The present invention relates to the use of peptide and non-peptide TPO receptor agonist compounds and an anti-clotting agent or agents, and optionally further active ingredients in the treatment of thrombocytopenia in a mammal, including a human.

The present invention relates to the in vivo administration of a non-peptide TPO receptor agonist and an anti-clotting agent or agents in the treatment of thrombocytopenia in a human.

The invention also provides for the use of a compound of Formula (I) and an anti-clotting agent in the manufacture of a medicament or combination for use in the treatment of thrombocytopenia in humans.

The invention also provides for the use of a compound of Formula (I) and an anti-clotting agent in the manufacture of a medicament for use in therapy.

The invention also provides for a pharmaceutical composition or combination for use in the treatment of thrombocytopenia which comprises a compound of Formula (I) and an anti-clotting agent and a pharmaceutically acceptable carrier.

The invention also provides for the use of a compound of Formula (VI) and an anti-clotting agent in the manufacture of a medicament or combination for use in the treatment of thrombocytopenia.

The invention also provides for the use of a compound of Formula (VI) and an anti-clotting agent in the manufacture of a medicament or combination for use in therapy.

The invention also provides for a pharmaceutical composition for use in the treatment of thrombocytopenia which comprises a compound of Formula (VI) and an anti-clotting agent and a pharmaceutically acceptable carrier.

In addition, the pharmaceutically active compounds of the present invention can be co-administered with further active ingredients, such as other compounds known to treat thrombocytopenia or prevent or lessen the incidence of blood clots.

Contemplated Equivalents—It will be appreciated by the person of ordinary skill in the art that the compounds of Formulas I and VI may also exist in tautomeric forms. For example, in Formula I, the double bond that is drawn between the two nitrogen atoms exists between the lower nitrogen atom and the AR substituent. Tautomeric forms of the compounds of Formulas I and VI are exemplified by the following Formula (X):

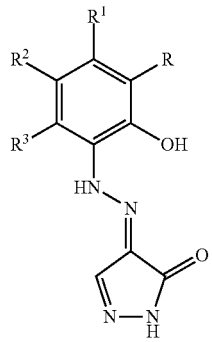

where the 'R' groups are as defined above. All such compounds are included in the scope of the invention and inherently included in the definition of the compounds of Formulas I and VI.

Without further elaboration, it is believed that one skilled in the art can, using the preceding description, utilize the present invention to its fullest extent. The following Examples are, therefore, to be construed as merely illustrative and not a limitation of the scope of the present invention in any way.

Experimental Details

Example 1

Capsule Composition

An oral dosage form for administering a compound or the present invention is produced by filing a standard two piece hard gelatin capsule with the ingredients in the proportions shown in Table I, below.

TABLE I

| INGREDIENTS | AMOUNTS |
|---|---|
| 3'-{N'-[1-(3,4-Dimethylphenyl)-3-methyl-5-oxo-1,5-dihydropyrazol-4-ylidene]hydrazino}-2'-hydroxybiphenyl-3-carboxylic acid | 25 mg |
| Mannitol | 55 mg |
| Talc | 16 mg |
| Magnesium Stearate | 4 mg |

Example 2

Injectable Parenteral Composition

An injectable form for administering a compound of the present invention is produced by stirring 1.5% by weight of 3-{N'-[1'-(3,4-dimethylphenyl)-3-methyl-5-oxo-1,5-dihydropyrazol-4-ylidene]hydrazino}-2-hydroxy-3'-(tetrazol-5-yl)biphenyl, in 10% by volume propylene glycol in water.

Example 3

Tablet Composition

The sucrose, microcrystalline cellulose and a non-peptide TPO agonist, as shown in Table II below, are mixed and granulated in the proportions shown with a 10% gelatin solution. The wet granules are screened, dried, mixed with the starch, talc and stearic acid, then screened and compressed into a tablet.

TABLE II

| INGREDIENTS | AMOUNTS |
|---|---|
| 1-(3-chloro-5-{[4-(4-chlorothiophen-2-yl)-5-(4-cyclohexylpiperazin-1-yl)thiazol-2-yl]carbamoyl}pyridine-2-yl)piperidine-4-carboxylic acid, | 20 mg |
| Microcrystalline cellulose | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A combination of agents comprising: 3'-{N'-[1-(3,4-Dimethylphenyl)-3-methyl-5-oxo-1,5-dihydropyrazol-4-ylidene]hydrazino}-2'-hydroxybiphenyl-3-carboxylic acid or a pharmaceutically acceptable salt thereof and an anti-clotting agent.

2. A combination according to claim 1, wherein the anti-clotting agent is selected from: heparin, warfarin, enoxaparin, aspirin, clopidogrel, ticlopidine, dipyridamole, prasugrel, tissue plasminogen activator, hirudin, lepirudin, argatroban, Ximelagatran, bivalirudin, dabigatran etexilate, rivaroxaban, apixaban, YM150, DU-176b, LY517717, PRT054021, rivaroxaban, fondaparinux, Idraparinux, tick anticoagulant peptide, antistatin, DX 9065a, Org31540/SR90107A, active-site blocked Factor IXa, monoclonal anti-Factor IXa, protein C derivative, recombinant thrombomodulin, tissue factor inhibitor, mutant tissue factor, factor Vila inhibitor (Factor VIIai), and Factor Vila/tissue factor blocker (TFPI, NAPc2).

3. A combination according to claim 2 wherein the compounds are administered orally.

4. A combination according to claim 2 wherein one compound is administered orally and one compound is administered parenterally.

* * * * *